March 28, 1950 O. E. FELTEN Plant Pat. 929
STRAWBERRY PLANT
Filed Feb. 25, 1949
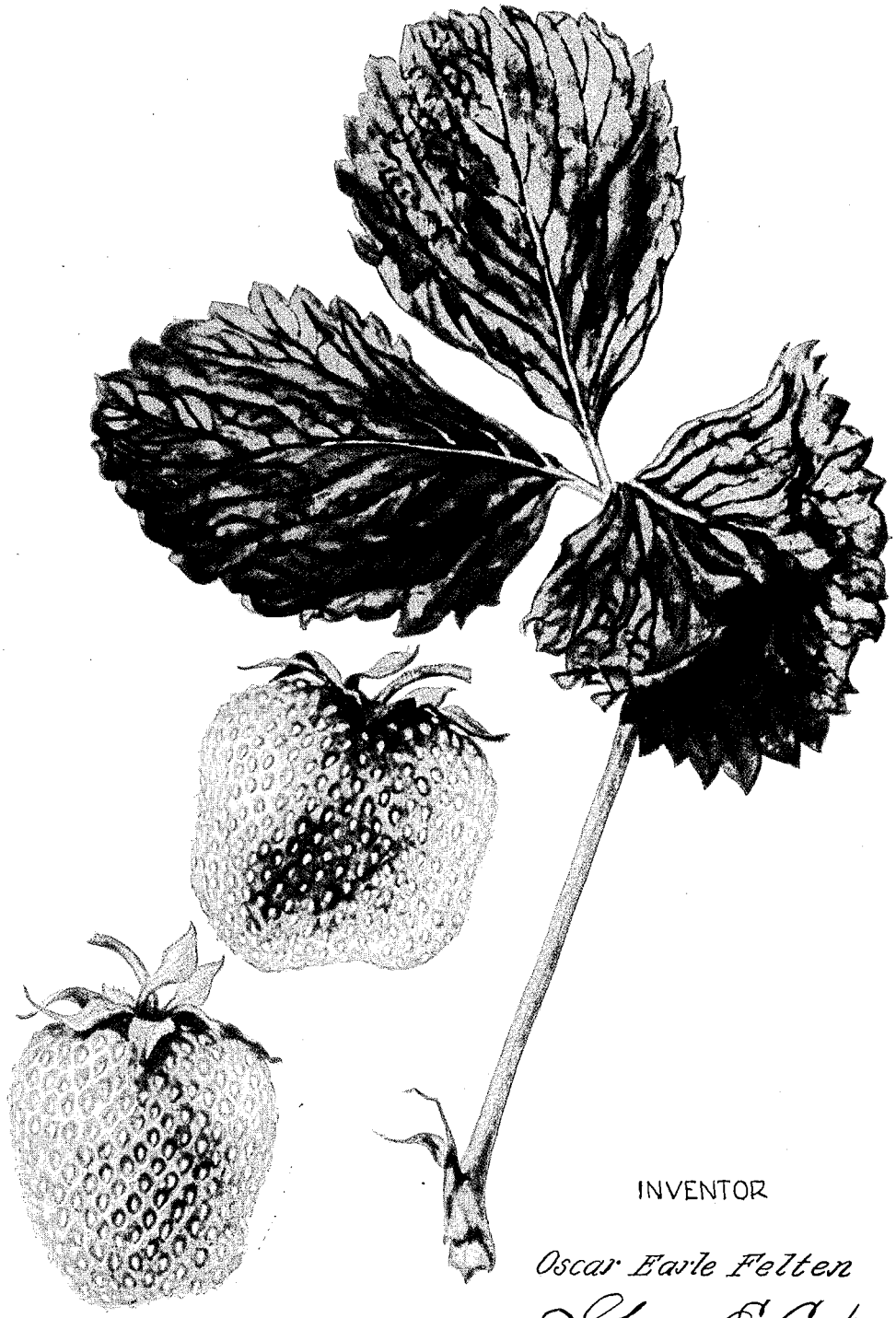
INVENTOR
Oscar Earle Felten
George E. Cook.
ATTORNEY Patented Mar. 28, 1950

Plant Pat. 929

UNITED STATES PATENT OFFICE

929

STRAWBERRY PLANT

Oscar Earle Felten, East Merchantville, N. J., assignor of one-half to William T. Wilkins, Moorestown, N. J.

Application February 25, 1949, Serial No. 78,440

1 Claim. (Cl. 47—62)

My present invention pertains to a new and distinct variety of strawberry plant, the object of my invention being the production of a healthy variety which grows well and produces large quantities of large berries which ship and stand up well in the commercial market. My present variety has all these as well as other good qualities, and asexual reproduction has proved them to be permanent.

My new variety originated as a seedling and is the result of inbreeding stock of Felten seedlings. Its immediate parents are unnamed seedlings of this stock, designated as No. 3001 and No. 3700 in our records. No. 3001 was produced by a cross between the varieties Premier and Marvel, which was crossed with Fairfax to produce No. 3700, it in turn having been crossed with the original No. 3001 to produce the present variety.

The illustrations accompanying the specifications show a typical berry of each of the types found on this variety, together with a leaf—all in approximately their true colors.

Following is a detailed description of the plant and fruit of my new variety, color plate references being in accordance with Ridgway's Color Standards and Nomenclature.

*The plant*

Type: Self-pollinating. Flowers "perfect."

Growth: Tall and vigorous, producing extra large plants which space themselves well in the row. Plants send out moderate number of long runners.

Root system: Strong, vigorous and very heavy, corresponding with the large plant growth.

Disease resistance: Plant is very healthy and apparently free from most diseases, even leaf-spot being rarely found.

Production: Very prolific producer of large berries.

Ripening: Midseason.

Foliage: Abundant; trifoliate; medium green with bronze edges. Leaflets almost round; approximately 3 inches long and 2¾ inches wide. Edge more scalloped than serrated.

Stems or petioles: Strong, heavy and upright; ciliate; 8 to 12 inches in length.

Fruit stems: Very heavy and strong. They hold berries upright thus keeping them clean and avoiding rot and mildew. The length of the fruit stem allows the berries to come just under the foliage, thus protecting them.

*Fruit*

Shape: Mostly wedge-shaped but some shouldered.

Size: Very large. 1¾ to 2¼ inches long and 5 to 6½ inches in circumference. Extra large berries are produced at the first of the season and they continue throughout the season to be larger than most berries of similar type.

Skin: Tough. Seeds not imbedded. The toughness of the skin and the position of the seeds continue to protect the berry in shipment.

Seeds: Yellow, large, prominent and closely spaced.

Color of skin: Dark red.

Calyx: Large, adheres well to berry, thus holding stem well. Hub slightly imbedded.

Aroma: Slight or faint.

Flesh:

*Texture.*—Firm but not hard. Fine-grained.

*Flavor.*—Mellow and pleasing.

*Color.*—Very dark red at extreme edge but very much lighter for the rest of the berry. A longitudinal cross-section shows an approximately white line about ¼ inch from the edge all around.

*Juiciness.*—Moderate.

*Comparison*

The known variety most like my new variety is called Sparkle. Following are the principal features of difference between the two varieties:

The plant of my variety is larger.

The berries of my variety are considerably larger at the beginning of the season and continue larger throughout the season.

The flavor of my berry is milder.

The flesh of my berry is not as hard.

Older berries of my variety do not discolor as much.

Skin of my berry is tougher.

Seeds of my berry provide more protection when shipping.

Having thus disclosed my invention, I claim:

The new and distinct variety of strawberry plant, substantially as herein shown and described, characterized particularly by its very large, vigorous and healthy plant; its heavy, upright fruit stems; its prolific production; and its very large berries of dark red color, mild flavor, firm but fine texture, and tough skin protected by prominent seeds.

OSCAR EARLE FELTEN.

No references cited.